United States Patent [19]
Slonim

[11] Patent Number: 6,116,426
[45] Date of Patent: Sep. 12, 2000

[54] EMERGENCY EYE KIT

[76] Inventor: Charles B. Slonim, 4444 E. Fletcher Ave., Suite D, Tampa, Fla. 33613

[21] Appl. No.: 09/416,182

[22] Filed: Oct. 11, 1999

[51] Int. Cl.[7] ..................................................... B65D 69/00
[52] U.S. Cl. ........................................... 206/570; 206/499
[58] Field of Search .................................... 206/223, 499, 206/570–572, 803, 561, 438, 440

[56] References Cited

U.S. PATENT DOCUMENTS

| | | | |
|---|---|---|---|
| 1,857,824 | 5/1932 | Scholz et al. ............................. | 206/572 |
| 5,011,020 | 4/1991 | Stevens et al. ........................... | 206/570 |
| 5,439,108 | 8/1995 | Lackie ...................................... | 206/499 |
| 5,848,700 | 12/1998 | Horn ........................................ | 206/570 |
| 5,931,304 | 8/1999 | Hammond ............................... | 206/570 |
| 5,979,658 | 11/1999 | Allen et al. .............................. | 206/570 |

*Primary Examiner*—Paul T. Sewell
*Assistant Examiner*—Luan K. Bui

*Attorney, Agent, or Firm*—Dennis L. Cook

[57] ABSTRACT

An emergency medical kit having a container with a hinged lid and a latch for use in organizing and protecting ophthalmic instruments and supplies, such as sterilized pads, drugs, extractors, lights, ointments, tape and other items needed by a physician or emergency personnel working under the auspices of a physician in rendering emergency medical assistance to a person suffering an eye injury. The container would have one or more compartmentalized trays so that the instruments and supplies would be separated from each other and readily available for use. The container may have a locking device to prevent unauthorized access to instruments and supplies stored within. The container would be lightweight and compact, so that it is readily portable and easily stored. It is contemplated for the present invention to be used in any location where a physician or emergency personnel is called upon to diagnose and treat someone who has suffered an eye injury, including, but not limited to, medical offices of non-ophthalmic physicians, accident sites, shopping malls, residences, sporting events, and camping facilities.

4 Claims, 4 Drawing Sheets

EMERGENCY EYE KIT

BACKGROUND

1. Field of Invention

This invention relates to first aid kits, specifically to an emergency medical kit containing instruments and supplies for a physician or emergency personnel working under the auspices of a physician, such as Emergency Medical Services (EMS) personnel, to use in an emergency situation to diagnose and treat someone who has suffered an eye injury. It is contemplated for the present invention to be used in any location where a physician or EMS personnel is called upon to diagnose and treat someone who has suffered an eye injury, including, but not limited to, medical offices of non-ophthalmic physicians, accident sites, shopping malls, residences, sporting events, and camping facilities.

2. Description of Prior Art

Adequate instruments and supplies to diagnose and treat eye injuries are almost always available to ophthalmic physicians when they are in an ophthalmic medical office or hospital setting. However, when physicians and optometrists are called upon to render assistance to those with eye injuries in non-ophthalmic medical offices and or in other locations remote from an ophthalmic medical office or a hospital, appropriate instruments and supplies may not be available. One example is when physicians at home are asked by neighbors to treat children with sports related, or other types of, eye injuries. Also, physicians may not have the appropriate instruments and supplies to render emergency assistance to those with eye injuries when they are called upon to render emergency assistance in public places, such as at accident sites, at concerts, in sports arenas and stadiums, and in shopping malls. It is not known to have an emergency medical kit containing specific ophthalmic instruments and supplies, for use by a physician or EMS personnel to render emergency medical assistance to a person with an eye injury in a location remote from an ophthalmic medical office or a hospital.

It is known for hospitals and some physician's offices to have portable examination carts to support eye examination devices, drugs and miscellaneous items, and which may be conveniently wheeled through a corridor from one location to another. Such an examination cart is disclosed in U.S. Pat. No. 4,095,859 to Decker (1978). The Decker examination cart also has an electrical power system, lamps, and lockable covers. Although portable, the Decker cart is too large and too bulky for a physician to use in remote locations for the emergency diagnosis and treatment of eye injuries. Also, the type of cart disclosed in the Decker patent would be too expensive for such use.

Many types of eye flush systems are also available for the emergency treatment of eye injuries. Some eye flush systems are portable and some, such as those found in laboratories, are positioned at permanent locations. A portable eye cup, which is oval-shaped to fit over an eye and which may be repeatedly filled with tap water, is commonly found in household medicine cabinets for eye-flushing purposes. More complex eye flush systems involve fountains which have nozzles to spray eye-flushing liquid into an eye to rinse it. Other eye flush systems involve reservoirs of eye-flushing liquid which have eye pieces or masks attached to them to cover the eye and direct eye-flushing liquid into the injured eye. U.S. Pat. No. 5,320,615 to Van Keuren (1994) discloses a portable eye flush device having a bladder of eye-flushing fluid attached to a mask. Also, some eye flush systems simply involve a flexible bottle of eye-flushing liquid with an eye-piece attached to it, which may be uncapped, inverted over an eye, and squeezed to dispense the eye-flushing liquid stored within into the eye to rinse it. All of these eye flush systems will dilute harmful liquids splashed into an eye, or rinse away foreign particles floating on the outer surface of an eye, but they will not extract an object lodged or stuck onto the surface of the eye, nor do such eye flush systems provide the appropriate supplies to cover and protect the eye after the rinsing procedure is concluded.

When the foreign particles which get into an eye are metallic, it is important to extract the metallic particles from the eye as soon as possible, especially metallic particles containing iron which can create rust deposits on the ocular surface. When metallic particles in an eye begin to rust, they require more extensive care to remove both the metallic foreign body and the rust deposits. Thus, it would be desirable to have an emergency eye kit containing the appropriate instruments and supplies available for physicians and EMS personnel to use in rendering emergency assistance to persons suffering eye injuries in locations remote from an ophthalmic medical office or a hospital, especially where the injuries involve foreign particles stuck onto the ocular surface.

SUMMARY OF INVENTION—OBJECTS AND ADVANTAGES

It is the primary object of this invention to provide an emergency medical kit containing the appropriate instruments and supplies for a physician or EMS personnel to use in rendering emergency medical assistance to a person suffering an eye injury in his or her office as well as in remote locations. A further object of this invention is to provide an emergency medical kit having the appropriate instruments and supplies to assist a physician or EMS personnel in diagnosing certain ocular conditions such as corneal and/or conjunctival abrasions. It is also an object of this invention to provide an emergency medical kit having instruments for a physician or EMS personnel to use in the extraction of superficial foreign particles from an eye. It is also an object of this invention to provide an emergency medical kit containing supplies for a physician or EMS personnel to use to protect an eye after rendering emergency assistance to the eye. A further object of this invention is to provide an emergency medical kit which will securely hold and protect prescription drugs, ophthalmic instruments and supplies so that they will be available for use by a physician or EMS personnel in rendering emergency medical assistance to people with eye injuries in medical offices as well as in remote locations. It is also an object of this invention to provide an emergency medical kit having ophthalmic instruments and supplies which are separated from each other and organized in a manner which allows a physician or EMS personnel immediate access to the exact instrument or supply needed for rendering emergency medical assistance to a person with an eye injury.

As described herein, properly manufactured and used, the present invention would provide a storage container with a hinged lid and a latch that would securely contain sterilized pads, drugs, extractors, lights, ointments, tape and other items needed for use by a physician or EMS personnel in rendering emergency medical assistance to a person suffering an eye injury. The container would have one or more compartmentalized trays so that the instruments and supplies would be separated from each other and readily available for use by a physician or EMS personnel in an emergency situation. Alcohol pads in the container could be used to disinfect all of the other instruments and supplies stored therein. The container could have a locking device to limit unauthorized access to the instruments and supplies. The container would be compact so that it could be easily stored in a portable medical bag, a physician's home, a motorized vehicle, or a medical office. It would also be made from lightweight materials so that it is easily portable.

The description herein provides preferred embodiments of the present invention but should not be construed as limiting the scope of the emergency eye kit invention. Variations in number, types, and amounts of medical supplies available for use in treating an injured eye, the number and types of ophthalmic instruments available for use in treating an injured eye, the size and shape of the outer container used for the ophthalmic instruments and supplies, the material from which the outer container and trays are made, the means of closing the outer container, whether or not a locking device is used, the means of locking the outer container, the organizational placement of the ophthalmic instruments and supplies within the outer container and trays, and the size, number and configuration of the trays used in the outer container, other than those shown and described herein, can be incorporated into the present invention. Thus the scope of the present invention should be determined by the appended claims and their legal equivalents, rather than the examples given.

DETAILED DESCRIPTION OF PREFERRED EMBODIMENTS

Figure 1:
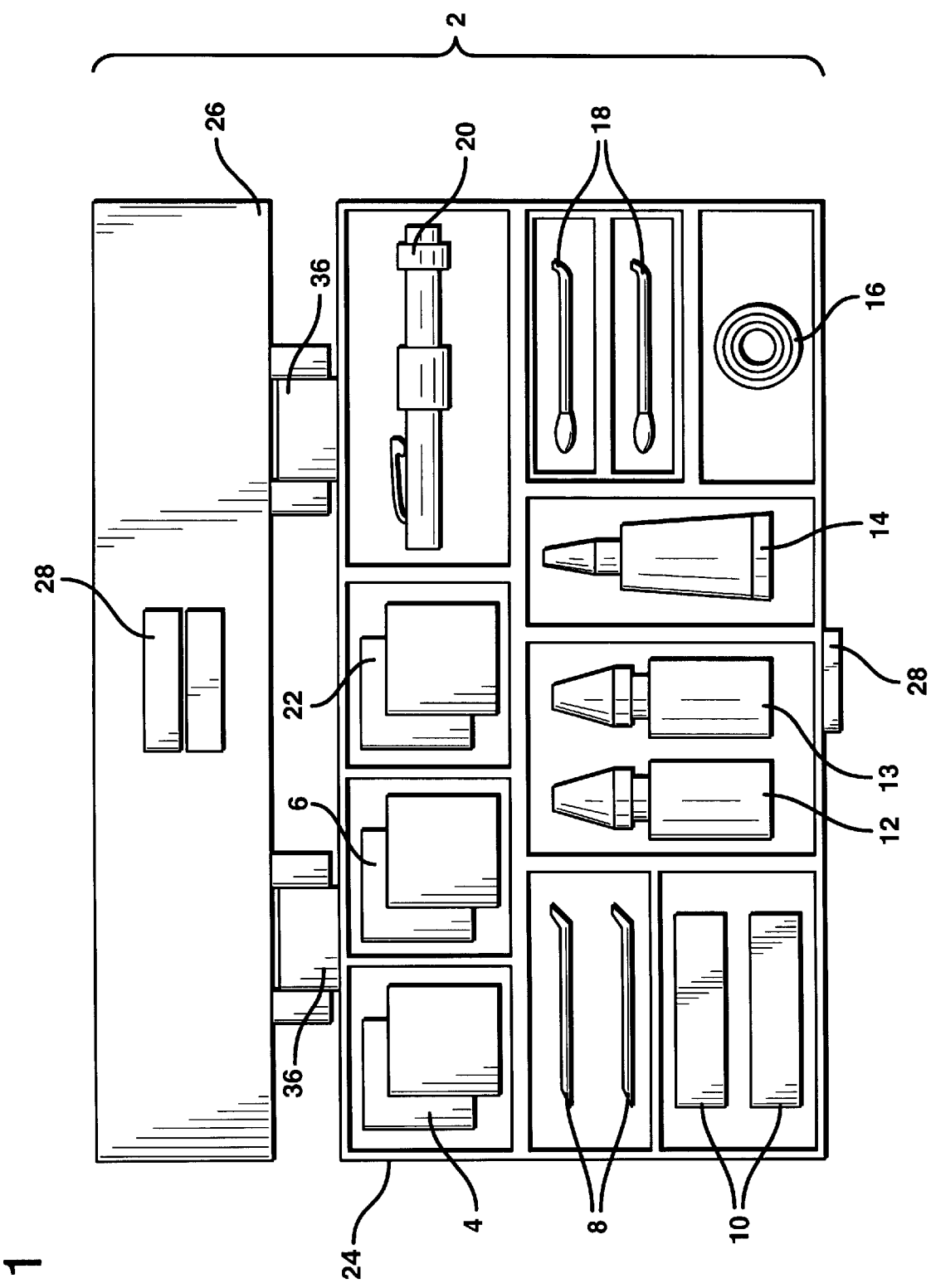
FIG. 1 is a top view of a first embodiment of the invention having an assortment of ophthalmic instruments and supplies contained therein.

FIG. 1 shows an emergency eye kit invention 2 having a bottom portion 24 and a lid 26. Lid 26 is attached to bottom portion 24 by hinges 36. Although FIG. 1 shows two hinges 36 connecting lid 26 to bottom portion 24, the use of hinges 36 is not critical to emergency eye kit invention 2. It is contemplated for emergency eye kit invention 2 to have any number of hinges 36, or other means of attaching lid 26 to bottom portion 24. FIG. 1 also shows a latch 28 for securing lid 26 to bottom portion 24 in a closed position. Latch 28, as shown in FIG. 1, is not critical to emergency eye kit invention 2. It is contemplated to have any means which securely closes lid 26 against bottom portion 24. Although not critical to emergency eye kit invention 2, it is also contemplated that a locking device (not shown) may be used with latch 28 to prevent unauthorized access to ophthalmic instruments and supplies stored in emergency eye kit invention 2. FIG. 1 shows a bottom portion 24, with compartments holding ophthalmic instruments and supplies to include sterile gauze pads 4, sterile eye pads 6, sterile alcohol pads 22, foreign body removers 8, cotton-tipped swabs 18, a pen-style light 20 to assist in examining the eye, lubricating eye drops 12, sterile ophthalmic antibiotic solution 13, sterile ophthalmic antibiotic ointment 14, sterile ophthalmic fluorescein strips 10, and medical adhesive tape 16. The exact number of ophthalmic instruments and supplies available for the emergency treatment of eye injuries is not critical to emergency eye kit invention 2. However, in the preferred embodiment, emergency eye kit invention 2 contains at least two sterile packages of 2-inch by 2-inch, 12-ply pads of U.S.P. type V11 gauze 4; at least two sterile packages each containing an oval eye pad 6 large enough to cover the eye and the area adjacent to the eye socket; at least two 2-ply, medium, individually wrapped alcohol prep pads 22 saturated with 70% isopropyl alcohol; at least one container of eye wash solution (not shown), at least one roll of ½-inch medical adhesive tape 16; at least one resealable flexible bottle with a dispensing cap containing sterile lubricating eye drops 12; at least one resealable flexible bottle of sterile ophthalmic antibiotic solution 13; at least one 3.5 gm. flexible tube of sterile ophthalmic antibiotic ointment 14; at least one tube of sterile ophthalmic anesthetic solution (not shown): at least two 1 mg. fluorescein sodium BP sterile ophthalmic strips 10; at least one pen-style light 20 approximately 5-inches long and ½-inch in diameter with a clip for attachment to a pocket; a least one removable cobalt filter (shown attached to pen-style light 20) for use on pen-style light 20 and with fluorescein ophthalmic strips 10 for detecting abrasions; at least one reusable plastic foreign body remover 8 approximately 5-inches long and ¼-inch in diameter with a beveled shovel end on one of its ends and a bent tip on its opposite end, and at least two individually wrapped cotton-tipped swabs 18 each approximately 2½ inches long and 3/32-inches in diameter and having an elongated center portion with an enlarged, softly padded oval portion on one of its ends. Also, in the preferred embodiment, all of the containers and packages are easily opened and the expendable supplies are positioned so that they may be easily inventoried for prompt replacement.

Figure 2:
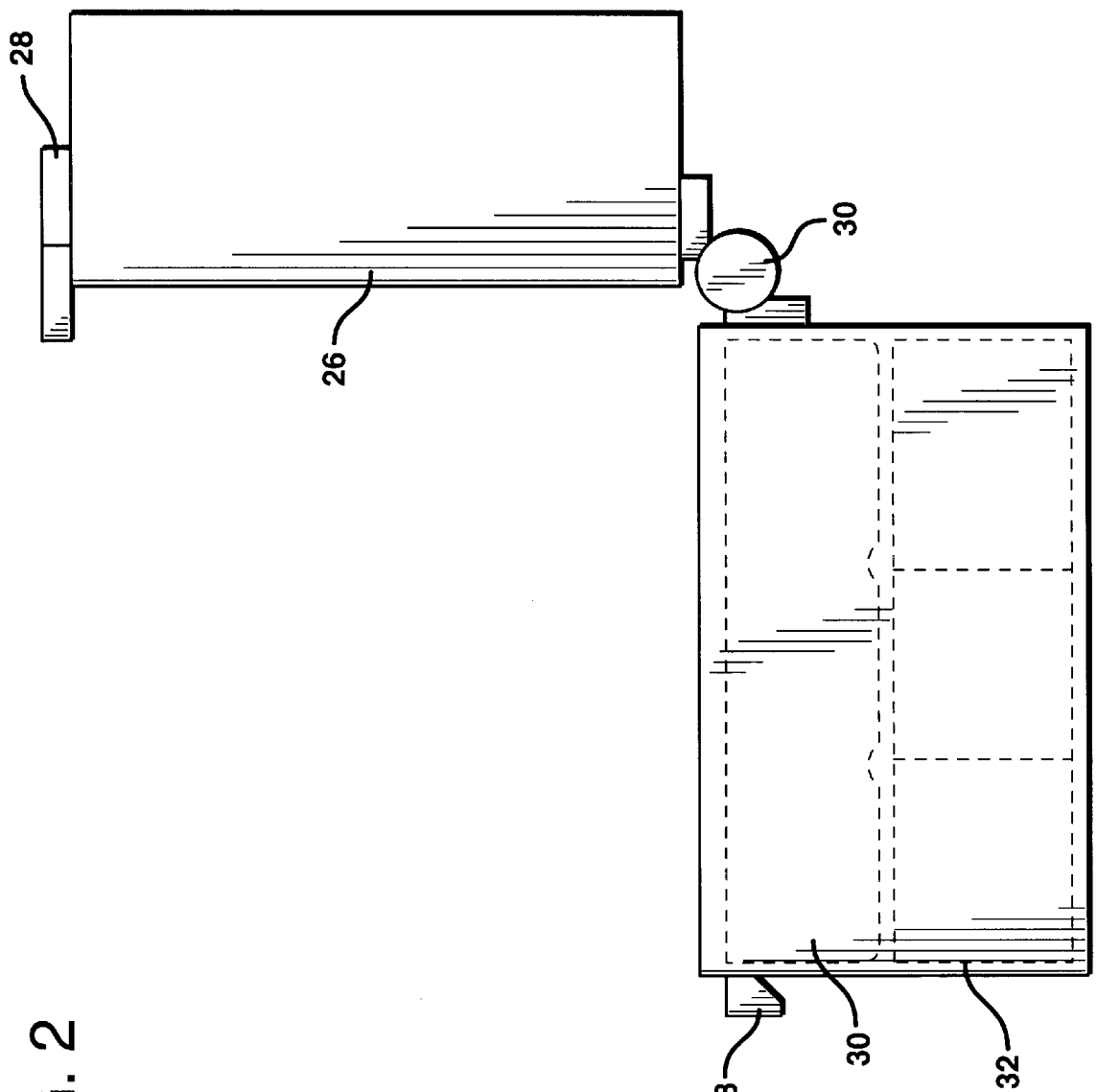
FIG. 2 is a side view of a second embodiment of the invention in an opened position showing location of compartments and trays.
Figure 3:
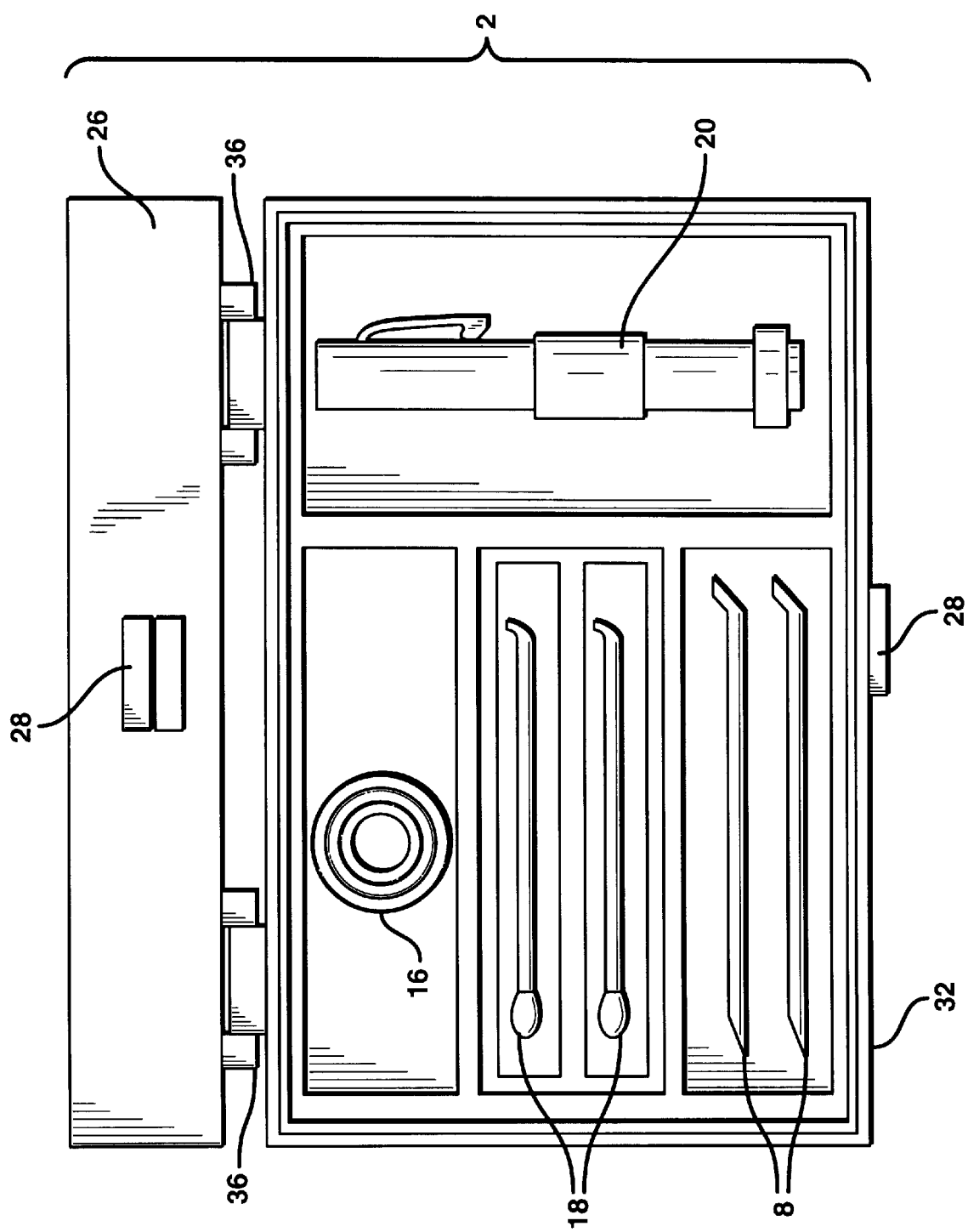
FIG. 3 is a view of the second embodiment having an assortment of ophthalmic instruments and supplies in a deep bottom section.
Figure 4:
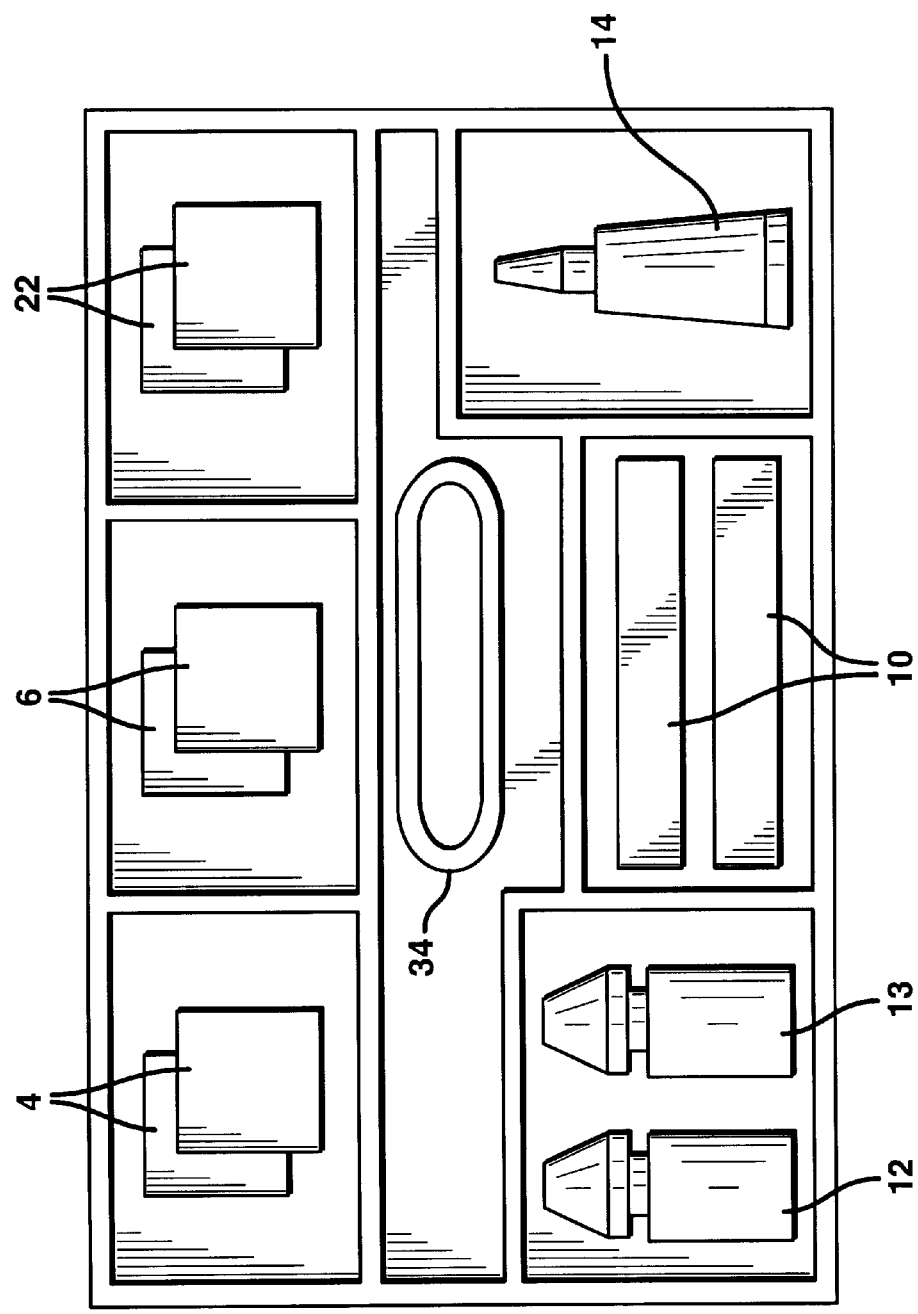
FIG. 4 is a top view of a removable top tray used in the deep bottom section of the second embodiment and containing an assortment of expendable supplies.

FIGS. 2, 3 and 4 shows an alternative embodiment of the emergency eye kit invention 2 having a deep bottom section 32 with compartments and space above the compartments for positioning one or more removable top trays 30. FIG. 3 shows ophthalmic instruments positioned within compartments in deep bottom section 32 to include foreign body removers 8, individually wrapped sterile swabs 18, a pen-style light 20 to assist in examining an eye, and ½-inch medical adhesive tape 16. FIG. 4 shows removable top tray 30 filled with expendable supplies to include sterile gauze pads 4, sterile eye pads 6, sterile alcohol pads 22, lubricating eye drops 12, sterile ophthalmic antibiotic solution 13, sterile ophthalmic antibiotic ointment 14, and sterile ophthalmic fluorescein strips 10. Positioning of such expendable supplies in removable top tray 30 lends visibility to them for inventory and replacement purposes so that emergency eye kit invention 2 will always have a full complement of instruments and supplies for use. Top tray 30 may have a handle 34 for ease in removing top tray 30 from deep bottom section 32.

Although not shown, it is also contemplated for emergency eye kit invention 2 to have a configuration other than the rectangular configuration shown in FIGS. 1, 2, 3, and 4, as long as alternate configurations are compact so as to be easily portable. The material from which top portion 26, bottom portion 24, removable top tray 30 and deep bottom section 32 are made is not critical to emergency eye kit invention 2. However, the material used for top portion 26, bottom portion 24, removable top tray 30 and deep bottom section 32 must be rigid, light in weight, easily molded for inexpensive construction, and impenetrable by liquids. In the preferred embodiment, top portion 26, bottom portion 24, removable top tray 30 and deep bottom section 32 are made out of plastic.

What is claimed is:

1. An emergency medical kit for use by a physician and emergency medical services personnel in diagnosing and treating eye injuries comprising a compact, lightweight container having a lid and a bottom portion with a hollow interior; a plurality of hinges for attaching said lid to said bottom portion; said lid movable between a plurality of opened positions and a closed position in which said lid is positioned securely against said bottom portion so as to seal said hollow interior; a plurality of latches for securing said lid to said bottom portion in said closed position; a plurality of compartmentalized trays positioned within said hollow interior; said compartmentalized trays containing at least one sterile package of gauze, at least one sterile package containing an oval eye pad large enough to cover an eye and the area adjacent to said eye, at least one alcohol prep pad saturated with isopropyl alcohol, at lease one container of eye wash solution, at least one roll of medical adhesive tape, at least one resealable flexible bottle containing sterile lubricating eye drops, at least one flexible tube of sterile ophthalmic antibiotic ointment, at least one flexible tube of sterile ophthalmic anesthetic solution, at least one resealable flexible bottle containing a sterile ophthalmic antibiotic solution, at least one fluorescein sodium BP sterile ophthalmic strip, at least one pen-style light, a least one removable cobalt filter for attachment to said pen-style light and for use with said fluorescein ophthalmic strip for detecting eye abrasions, at least one foreign body remover, and at least one sterile cotton-tipped swab so that said emergency medical kit is easily portable and said physician and said emergency medical services personnel may easily store and have ready for emergency use said emergency medical kit to diagnose and treat eye injuries.

2. The emergency medical kit of claim 1 wherein said emergency medical kit has a configuration such that all of said trays stack vertically within said hollow interior.

3. The emergency medical kit of claim 1 wherein at least one of said trays has a handle.

4. The emergency medical kit of claim 1 further comprising locking means connected to at least one of said latches.

* * * * *